United States Patent [19]

Harjung et al.

[11] Plant 4,828

[45] Mar. 2, 1982

[54] VARIEGATED LEMON TREE

[76] Inventors: Milton K. Harjung; Cameron Harjung, both of 5644 Durango Rd., Riverside, Calif. 92506

[21] Appl. No.: 111,112

[22] Filed: Jan. 10, 1980

[51] Int. Cl.[3] ..... A01H 5/03

[52] U.S. Cl. ..... Plt./45

[58] Field of Search ..... Plt./45

*Primary Examiner*—Robert E. Bagwill

*Attorney, Agent, or Firm*—Lyon & Lyon

[57] ABSTRACT

A variegated lemon tree particularly adapted for home use as an ornamental plant which displays an unusually wide variety of colors and color patterns.

3 Drawing Figures

BACKGROUND

This invention relates to a new and distinct variety of variegated lemon tree, the novel characteristics of which reside particularly in the color patterns and the multiplicity of colors displayed by both the new and the mature leaves.

The new lemon tree originated from a sport limb on a Lisbon type lemon tree in a cultivated lemon grove near Tustin, Calif. The limb was first discovered in 1970 by Milton K. Harjung. Thereafter, the new variety was successfully asexually reproduced by Milton K. Harjung and Cameron R. Harjung by budding on several citrus root stocks. This resulted in several progeny trees which have continually displayed the growth and color characteristics typical of that found on the parent sport limb.

An interesting characteristic of the tree is the vivid display of colors on the leaves. Oftentimes the leaf is equally and sharply divided with one half displaying a green color and the other half displaying a yellow color. Other leaves include a wide variety of yellow and green colors without any distinct division therebetween. Another interesting characteristic is the striped color pattern of the fruit and the wood. The wood displays stripes of white and green colors. Still another characteristic of the tree is its vigorous growth.

Other distinctive characteristics of the new variety are exemplified in the accompanying illustrations.

TECHNICAL DESCRIPTION

Figure 1:
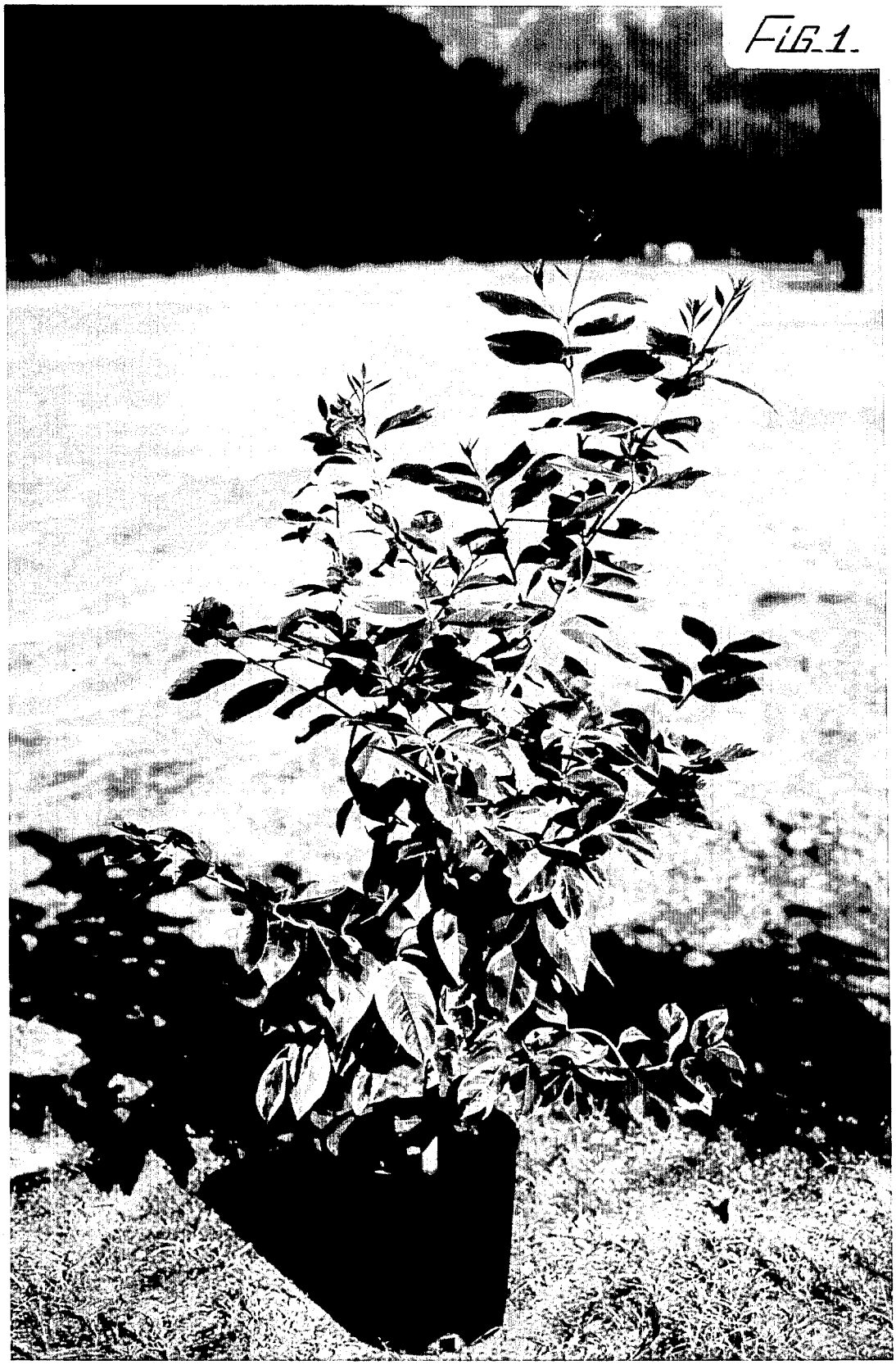
FIG. 1 shows an entire tree.
Figure 2:
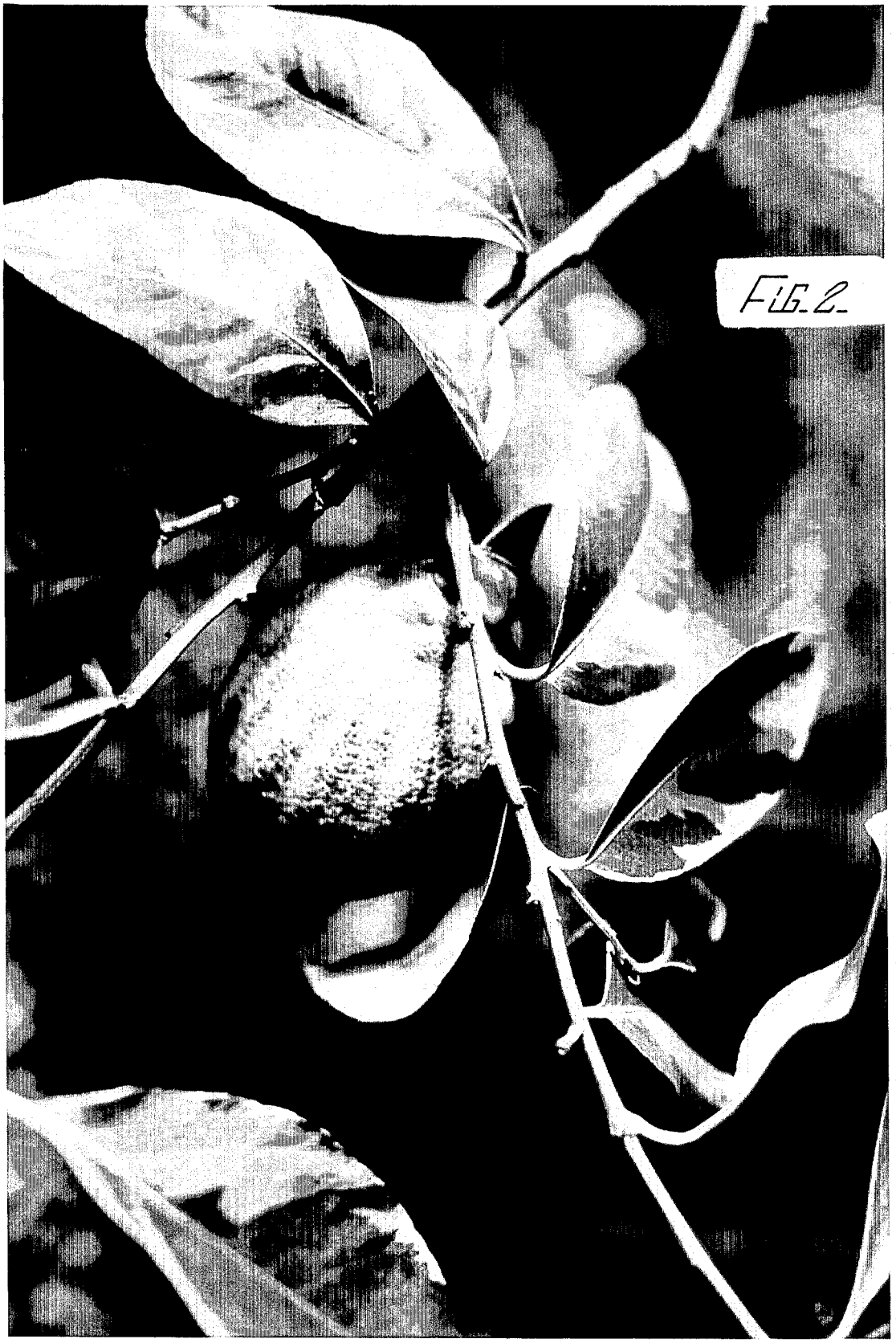
FIG. 2 shows a single whole fruit and the wood of the new variety, illustrating the color pattern of the fruit and wood.
Figure 3:
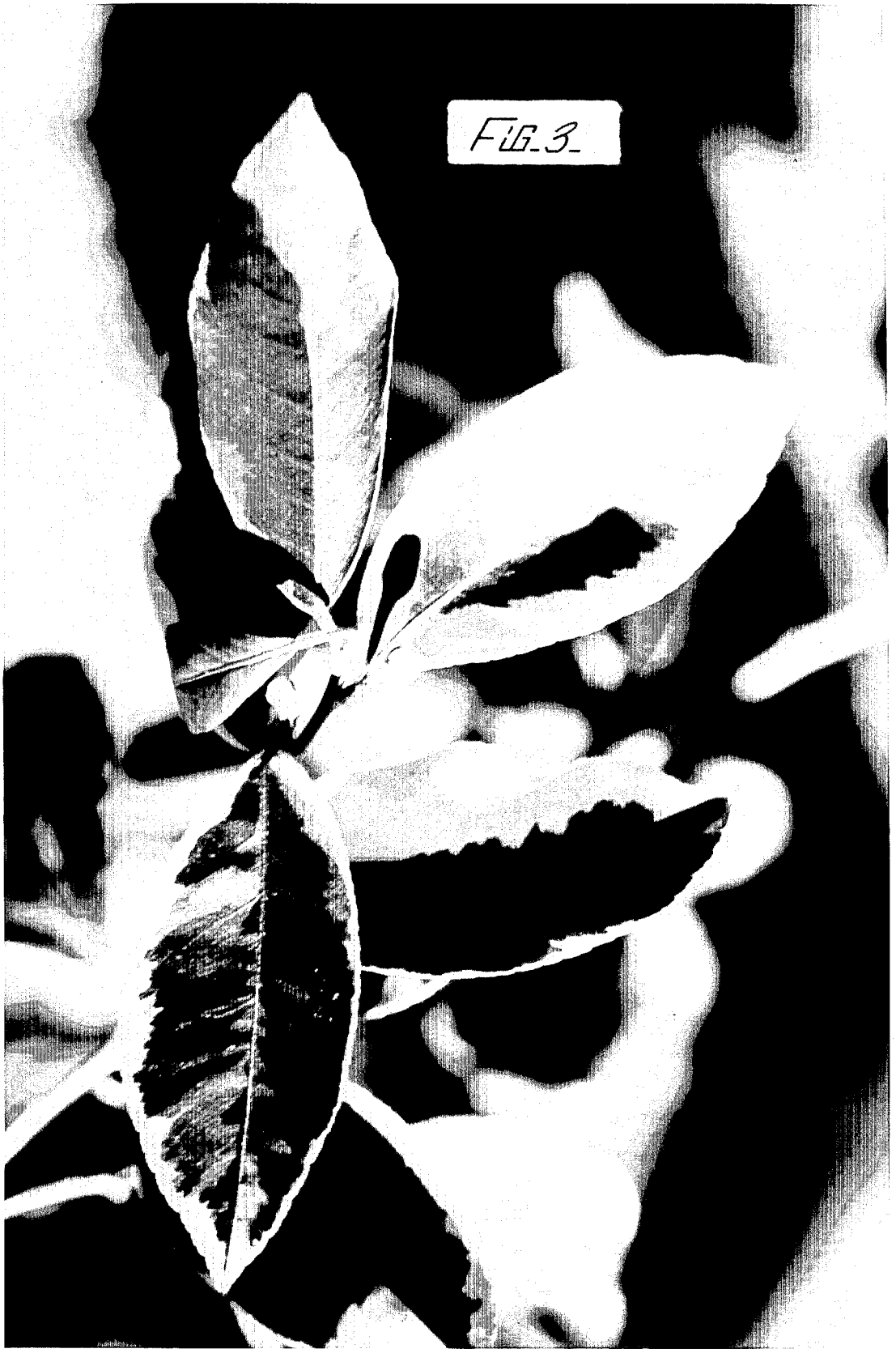
FIG. 3 shows in closeup several leaves of the new variety illustrating the various colors and color patterns found on the leaves.

The following is a description in some detail of the new variety of variegated lemon tree.

Tree:

*Shape.*—Spherical to conical; growth upright.

*Size.*—Small to medium.

*Growth.*—Dense; vigorous branches tend to grow out, upward beyond the trees' general periphery; abundant axillary and accessory bud development.

Flower:

*Size.*—Slightly smaller than Lisbon lemon in both length and diameter.

*Season.*—Twelve months in citrus growing areas.

*Ovary.*—Very slow development following fertilization.

Leaves:

*Shape and size.*—Large ovate; similar to Lisbon; except larger, slower developing leaves result when budded on slower growing root stocks.

*Color.*—Typical leaves include shades of yellow and green; yellow shades include, from the British Color Code (Ridgway Repertoire, by Ostwald): Barium yellow, plates 503/1, 503/0; Empire yellow, plate 603/0; Aureolin, please 3/3 and 3/2; Lemon yellow, plate 4/2; Buttercup yellow, plate 5/2; Indian yellow, plate 6/1; and Dresden yellow, plate 64/3. Green shades include Spinach green, plate 0960/0; 0960/1, 0960/2, 0960/3; Scheeles green, plates 806/2 and 806/3; Willow green, plates 000862/1 and 000862/2; Fern green 0868/0, 0862/1 and 0862/2; Chartreuse green, plates 663/0 and 663/1; Parsley green, plate 00962/1; Sage green, plates 000861/1, 000861/2 and 000861/3; Lettuce green, plate 861/1; and Pea green, plate 61/3.

Fruit, external characteristics:

*Color.*—Shades of green and yellow as identified in the description of the leaves. Definite green stripes on a background of a yellow shade similar to Lisbon during at least the developmental period, becoming similar to Lisbon upon maturity. Approximately 10–20% of the mature fruit retain the green striping of the immature fruit.

*Surface.*—Fairly smooth to pebbly. Inconspicuously ribbed.

*Shape.*—Round to oval elliptical or ellipsoid.

*Size.*—Generally, diameter: 2"–2.5", length: 2"–3.5".

*Base.*—Pronounced protruding nipple.

*Calyx.*—Medium in size, even or slightly depressed.

*Stem.*—Strong, usually $\frac{1}{4}$"–$\frac{3}{8}$" long.

*Apex.*—Gradually rounded, usually into a large, protruding nipple.

*Aerole.*—Irregular furrow at base of nipple, frequently deeper on one side than the other, forming a side wrinkle.

*Stylar scar.*—After fertilization, petals fall and pistil is visibly attached to ovary.

Fruit, internal characteristics:

*Rind.*—Finely pitted, slightly rugose and thin.

*Oil glands.*—Large globose to obovoid primary glands, surface depressed.

*Oil.*—0.18% of rind.

*Glandular layer.*—Approximately one-third the thickness of the rind.

*Mesocarp* (*albedo*).—White, vesicles spindle shape, long and slender.

*Axis.*—Small, solid, 3/16"-5/16" diameter.

*Segments.*—Generally between seven and ten.

*Pulp.*—Tender, fine grained, pale greenish yellow.

*Juice.*—Abundant, clear, high quality as citric acid, ph 2.7, acidity 4.6%.

*Seeds.*—Typical shape to broadly club shaped, ranging in number from few to ten or more.

The above described new variety of variegated lemon tree displays a multiplicity of colors and unusual color patterns on the leaves, fruit and wood. The wide variety of colors and distinct color patterns displayed by the tree make it a particularly desirable ornamental plant for use in home patios and backyard landscaping.

We claim:

1. A new and distinct variety of variegated lemon tree characterized particularly by the variety of colors and the color patterns displayed by the leaves, fruit and wood thereof.

* * * * *